(12) United States Patent
Shimizu et al.

(10) Patent No.: US 11,166,807 B2
(45) Date of Patent: Nov. 9, 2021

(54) PHAKIC INTRAOCULAR LENS

(71) Applicant: MUSASHINO LENS RESEARCH, INC., Tokyo (JP)

(72) Inventors: Kimiya Shimizu, Musashino (JP); Kazuhiko Onuma, Sodegaura (JP)

(73) Assignee: MUSASHINO LENS RESEARCH, INC., Tokyo (JP)

( * ) Notice: Subject to any disclaimer, the term of this patent is extended or adjusted under 35 U.S.C. 154(b) by 295 days.

(21) Appl. No.: 16/204,946

(22) Filed: Nov. 29, 2018

(65) Prior Publication Data
US 2019/0183634 A1    Jun. 20, 2019

Related U.S. Application Data

(62) Division of application No. 15/329,140, filed as application No. PCT/JP2014/069742 on Jul. 25, 2014, now abandoned.

(51) Int. Cl.
*A61F 2/16* (2006.01)

(52) U.S. Cl.
CPC .............. *A61F 2/1602* (2013.01); *A61F 2/16* (2013.01); *A61F 2/1601* (2015.04); *A61F 2/161* (2015.04); *A61F 2/1654* (2013.01); *A61F 2250/0053* (2013.01)

(58) Field of Classification Search
CPC ...... A61F 2/161; A61F 2/1601; A61F 2/1602; A61F 2/1654; A61F 2/1656
See application file for complete search history.

(56) References Cited

U.S. PATENT DOCUMENTS

| | | | |
|---|---|---|---|
| 4,585,456 A | 4/1986 | Blackmore |
| 4,769,035 A | 9/1988 | Kelman |
| 5,098,444 A | 3/1992 | Feaster |
| 5,121,980 A | 6/1992 | Cohen |
| 5,480,428 A | 1/1996 | Fedorov et al. |
| 6,197,057 B1 | 3/2001 | Peyman et al. |
| 6,829,093 B1 | 12/2004 | Nakai |
| 2001/0051826 A1 | 12/2001 | Bogaert et al. |
| 2003/0014107 A1 | 1/2003 | Reynard |

(Continued)

FOREIGN PATENT DOCUMENTS

| | | |
|---|---|---|
| CN | 1406120 A | 3/2003 |
| CN | 101686856 A | 3/2010 |

(Continued)

OTHER PUBLICATIONS

Extended European Search Report for related EP App No. 14897929.7 dated Mar. 5, 2018, 7 pgs.

(Continued)

*Primary Examiner* — Jerrah Edwards
*Assistant Examiner* — Christine L Nelson
(74) *Attorney, Agent, or Firm* — Procopio, Cory, Hargreaves & Savitch LLP

(57) ABSTRACT

The present invention is a phakic intraocular lens for implantation between an iris and a crystalline lens. The phakic intraocular lens includes a diffraction grating 5 disposed in a lens central part 2 and having circular, coaxial grooves formed thereon, and a support part 3 disposed outside the diffraction grating 5 and supporting the diffraction grating 5. A hole 6 is formed in the center of the diffraction grating 5.

3 Claims, 5 Drawing Sheets

(56) References Cited

U.S. PATENT DOCUMENTS

| | | |
|---|---|---|
| 2003/0097177 A1 | 5/2003 | Tran |
| 2004/0085511 A1* | 5/2004 | Uno .................. A61F 2/1602 351/159.02 |
| 2006/0116764 A1* | 6/2006 | Simpson ................ A61F 2/164 351/159.11 |
| 2008/0097599 A1 | 4/2008 | Rozakis et al. |
| 2008/0300679 A1 | 12/2008 | Altmann |
| 2011/0098811 A1 | 4/2011 | Hong et al. |
| 2011/0267693 A1* | 11/2011 | Kobayashi ........... G02B 5/1885 359/569 |
| 2012/0323319 A1 | 12/2012 | Cohen et al. |
| 2013/0268071 A1 | 10/2013 | Vilupuru et al. |
| 2014/0168774 A1 | 6/2014 | Zhao |

FOREIGN PATENT DOCUMENTS

| | | |
|---|---|---|
| CN | 102791222 A | 11/2012 |
| CN | 103006351 A | 4/2013 |
| EP | 2378319 A1 | 10/2011 |
| EP | 2403429 A1 | 1/2012 |
| JP | 2004147770 A | 5/2004 |
| JP | 2007534360 A | 11/2007 |
| JP | 2013508095 A | 3/2013 |
| WO | 2005058204 A1 | 6/2005 |
| WO | 2014100480 A1 | 6/2014 |

OTHER PUBLICATIONS

Office Action for related JP App No. 2016-535618 dated Oct. 17, 2017, 4 pgs.

Office Action for related CN App No. 201480080244.3 dated Oct. 10, 2017, 12 pgs.

Office Action for related KR App No. 10-2017-7001990 dated Oct. 30, 2017, 7 pgs.

International Search Report and Written Opinion for related PCT App No. PCT/JP2014/069742 dated Aug. 19, 2014, 6 pgs.

\* cited by examiner

PHAKIC INTRAOCULAR LENS

This application is a Divisional of U.S. application Ser. No. 15/329,140, filed Jan. 25, 2017, which is a U.S. National Stage Entry of PCT Application No. PCT/JP2014/069742, filed on Jul. 25, 2014, the contents all of which are incorporated herein by reference.

TECHNICAL FIELD

The present invention relates a phakic intraocular lens with a diffraction grating.

BACKGROUND ART

A phakic intraocular lens is recognized as a way of correcting visual impairment, besides eyeglasses and contact lenses. A lens for implantation between the iris and the crystalline lens is known as this phakic intraocular lens.

A phakic intraocular lens described in Patent Literature 1 includes a central optic part, a peripheral haptic part, and a penetrating hole having an anterior orifice and a posterior orifice, and the groove is arranged at the border of, or outside, the central optic part.

CITATION LIST

Patent Literature

Patent Literature 1: Japanese Translation of PCT International Application No. 2007-534360

SUMMARY OF INVENTION

Technical Problem

When a phakic intraocular lens is a convex lens, the central part of the lens is thick. Thus, providing a hole in the central part of the convex lens impairs the optical performance of the lens.

In a conventional phakic intraocular lens in which a hole is formed not at the center but at a periphery part, the hole gets blocked by the iris upon pupil contraction. This hinders the flow of aqueous humor.

The present invention aims to provide a phakic intraocular lens which allows reduction in lens thickness and facilitates the flow of aqueous humor.

Solution to Problem

To solve the problems described above, a phakic intraocular lens according to the present invention is a phakic intraocular lens for implantation between an iris and a crystalline lens, comprising: a diffraction grating disposed in a central part of the lens, the diffraction grating having circular, coaxial grooves formed thereon; and a support part that is disposed outside the diffraction grating and supports the diffraction grating. In the phakic intraocular lens, a hole is formed in a center of the diffraction grating.

DESCRIPTION OF EMBODIMENTS

A phakic intraocular lens according to Embodiment 1 of the present invention is described in detail below with reference to the drawings.

First Embodiment

Figure 1:
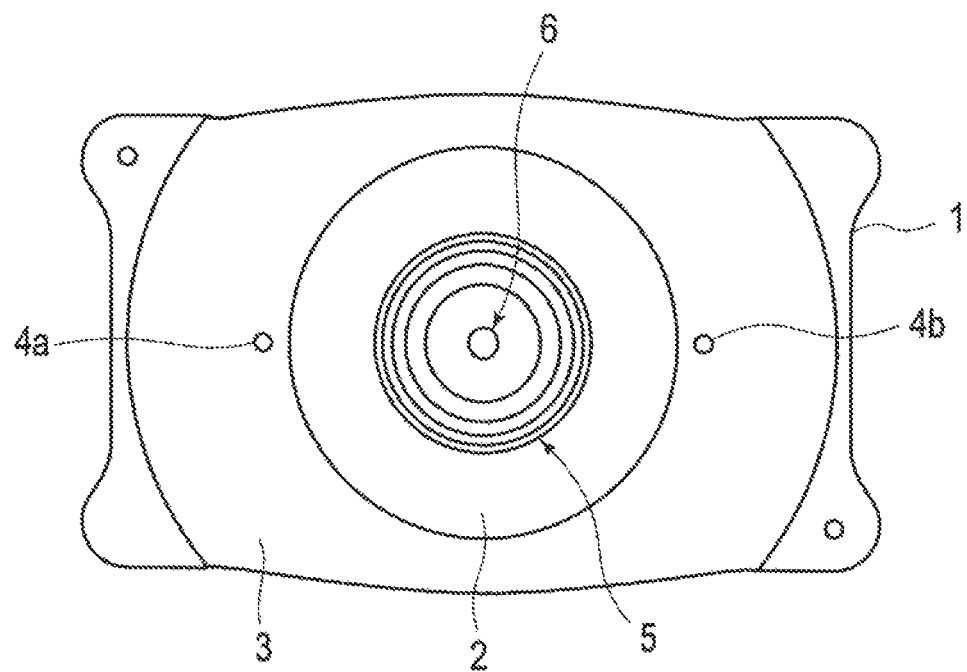
FIG. 1 is a diagram showing the configuration of a phakic intraocular lens according to Embodiment 1 of the present invention.

FIG. 1 is a diagram showing the configuration of a phakic intraocular lens according to Embodiment 1 of the present invention. A phakic intraocular lens 1 according to Embodiment 1 of the present invention is made from a copolymer of collagen, namely Collamer, and is implanted between the iris and the crystalline lens. The phakic intraocular lens 1 includes: a diffraction grating 5 which is disposed in a lens central part 2 and has coaxial grooves formed thereon; and a support part 3 which is disposed outside the diffraction grating 5 and supports the diffraction grating 5.

Reference numerals 4a and 4b indicate markings on the phakic intraocular lens, and they are provided outside the lens central part 2.

A circular hole 6 is formed in the center of the diffraction grating 5. The hole 6 is 0.25 mm to 0.5 mm in diameter.

Figure 2:
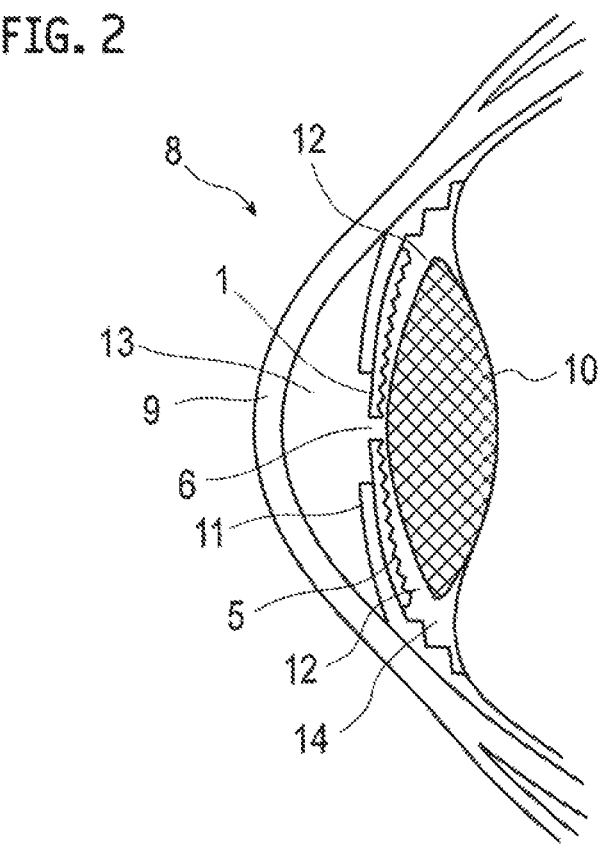
FIG. 2 is a sectional side view of an eye having the phakic intraocular lens according to Embodiment 1 of the present invention.

FIG. 2 is a sectional side view of an eye having the phakic intraocular lens according to Embodiment 1 of the present invention. As shown in FIG. 2, an eye 8 has a cornea 9, a crystalline lens 10, an iris 11, an anterior chamber 13, and a posterior chamber 14. The phakic intraocular lens 1 is implanted between the iris 11 and the crystalline lens 10. A gap 12 is provided between the phakic intraocular lens 1 and the crystalline lens 10. Aqueous humor in the posterior chamber 14 flows into the anterior chamber 13 through the gap 12 and the hole 6 in the diffraction grating 5.

Figure 3:
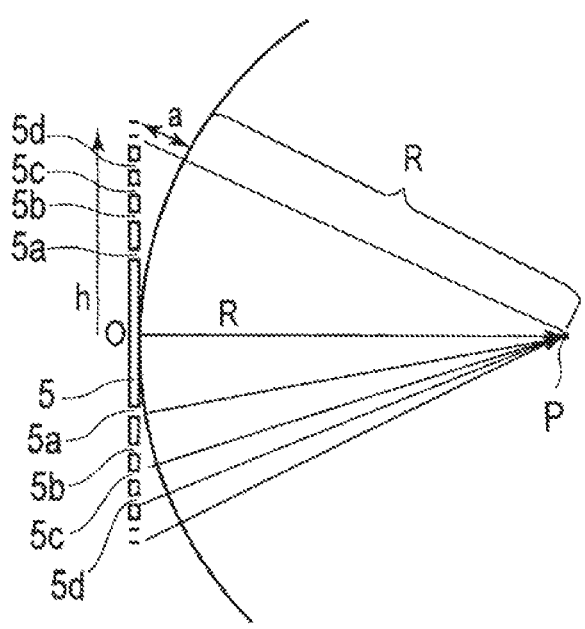
FIG. 3 is a diagram schematically showing the configuration of a diffraction grating of the phakic intraocular lens according to Embodiment 1 of the present invention, the diffraction grating having grooves formed thereon.

FIG. 3 is a diagram schematically showing the configuration of the diffraction grating of the phakic intraocular lens according to Embodiment 1 of the present invention, the diffraction grating having grooves formed thereon. FIG. 3 shows a basic configuration of a diffraction grating, and the grooves are shown as slits.

As shown in FIG. 3, the diffraction grating 5 has circular, coaxial grooves 5a to 5d formed thereon. The grooves 5a to 5d are formed such that the farther an interval between the grooves is from the center of the diffraction grating 5, the smaller the interval is. Specifically, the interval between the groove 5b and the groove 5c is smaller than the interval between the groove 5a and the groove 5b, and the interval between the groove 5d and the groove 5c is smaller than the interval between the groove 5b and the groove 5c. A height h from the center O of the diffraction grating 5 to each of the circular, coaxial grooves 5a to 5d is expressed by Formula (1):

$$h=(2Rm\lambda)^{1/2} \quad (1)$$

where λ is the wavelength of light, m is an integer, and R is the distance between the center O of the diffraction grating 5 and a focal point P. When m is 1, the height h is the distance between the center O to the groove 5a. When m is 2, the height h is the distance between the center O to the groove 5b. The same rule applies to the rest of the grooves, as well.

Figure 4:
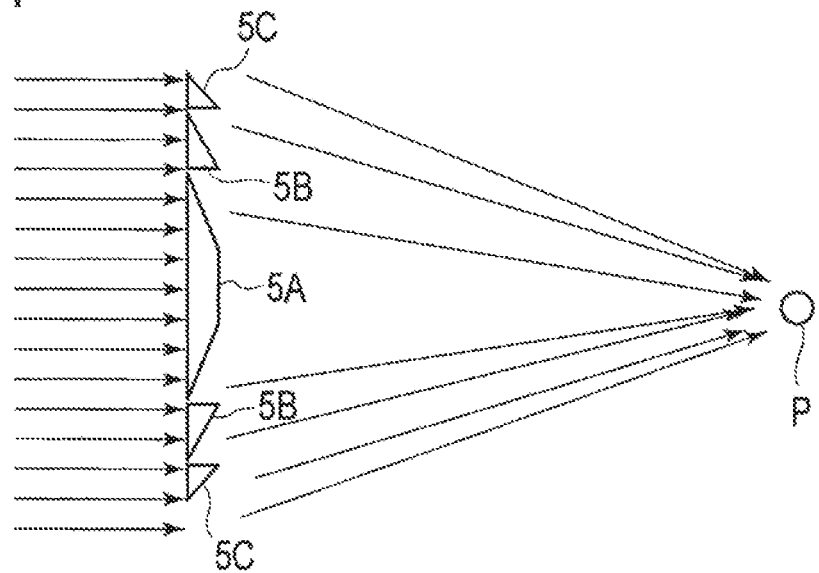
FIG. 4 is a diagram illustrating a single focal point formed by the diffraction grating of the phakic intraocular lens according to Embodiment 1 of the present invention, the diffraction grating having serrated grooves formed thereon.
Figure 5:
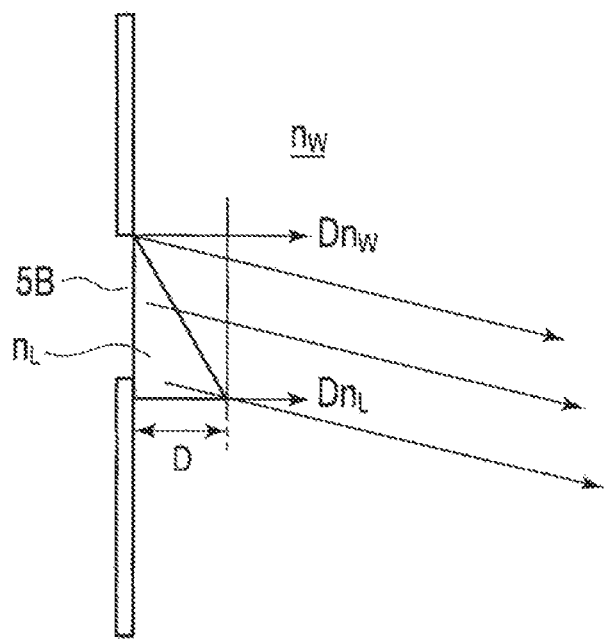
FIG. 5 is a diagram showing in detail the diffraction grating shown in FIG. 4 having the serrated grooves formed thereon.

FIG. 4 is a diagram illustrating a single focal point formed by the diffraction grating of the phakic intraocular lens according to Embodiment 1 of the present invention, the diffraction grating having serrated grooves formed thereon. FIG. 5 is a diagram showing in detail the diffraction grating shown in FIG. 4 having the serrated grooves formed thereon.

Serrated portions 5A to 5C are formed in the grooves to provide the diffraction grating 5 with a function as a lens. The serrated portions 5A to 5C are formed circularly and coaxially, the serrated portion 5B being narrower than the serrated portion 5A, the serrated portion 5C being narrower than the serrated portion 5B.

The index of refraction of each of the serrated portions 5A to 5C is indicated by nL, and the index of refraction of an area other than the serrated portions 5A to 5C is indicated by nW. The index of refraction nL is set to be larger than 1 to slow down the passage of light.

In the diffraction grating 5 shown in FIG. 4 having the serrated grooves formed thereon, all the phrases coincide, and a single focal point P is obtained. To obtain this signal focal point P, light passing through the upper part of the serrated portion 5B and light passing through the lower part of the serrated portion 5B need to have a phase difference of exactly one wavelength. Thus, since length×index of refraction=optical path length, Formula (2) holds true:

$$D(nL-nW)=\lambda \quad (2)$$

A height D is 4.4 μm when the wavelength λ is 0.546 μm (e-line), nL is 1.46 (the index of refraction of the lens), and nW is 1.336 (the index of refraction of aqueous humor). The height D of each of the serrated portions 5A to 5C is also 4.4 μm.

Figure 6:
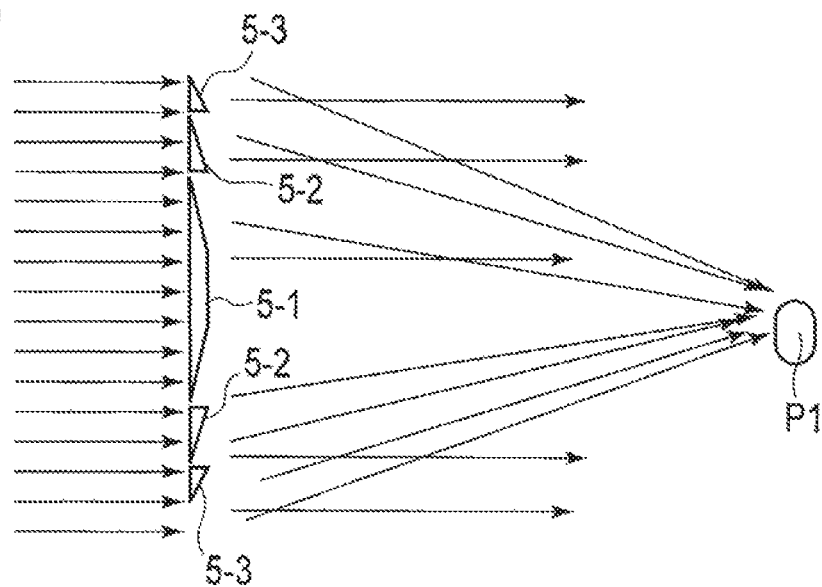
FIG. 6 is a diagram illustrating two focal points formed by a diffraction grating of a conventional phakic intraocular lens having serrated grooves.
Figure 7:
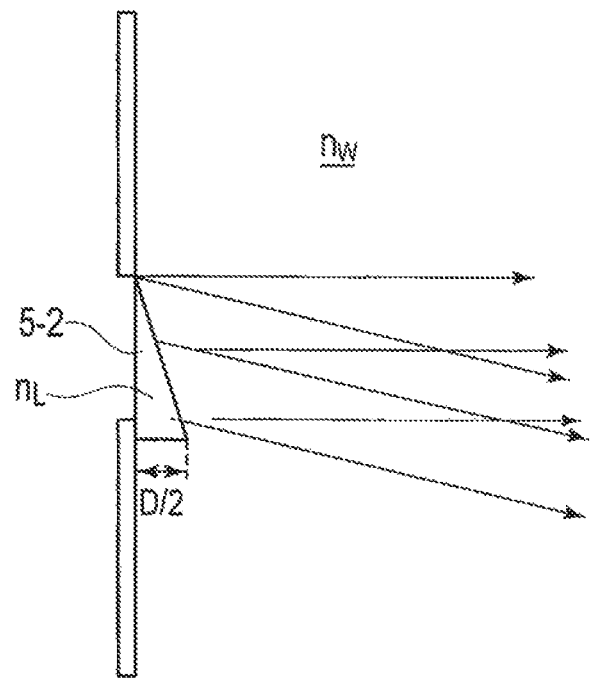
FIG. 7 is a diagram showing in detail the diffraction grating of the conventional phakic intraocular lens having the serrated grooves.

FIG. 6 is a diagram illustrating two focal points formed by a diffraction grating in a conventional phakic intraocular lens having serrated grooves formed thereon. FIG. 7 is a diagram showing in detail the diffraction grating of the conventional phakic intraocular lens having the serrated grooves formed thereon.

In FIG. 6, serrated portions 5-1 to 5-3 are formed in the grooves. The serrated portions 5-1 to 5-3 are formed such that not all the phases coincide, so that two focal points are obtained. Parallel light beams reinforce each other, and light beams that superpose due to the reduced height D weaken each other in intensity. The following Formula (3) for the height D holds true when the ratio of intensity between light distributed to one of the two focal points and light distributed to the other one focal point is 5:5:

$$D(nL-nW)=0.5\lambda. \quad (3)$$

When the indexes of refraction nL and nW and the wavelength λ for the two-focal-point case are set to the same values as those for the single-focal-point case, the height D is 2.2 μm. Hence, when the height of each of the serrated portions 5A to 5C shown in FIG. 4 is D, the height of each of the serrated portions 5-1 to 5-3 shown in FIG. 6 is D/2.

In the phakic intraocular lens 1 according to Embodiment 1 in which the diffraction grating 5 having the circular, coaxial grooves formed thereon is disposed in the lens central part 2, the diffraction grating 5 functions as a convex lens, contributing reduction in the thickness of the phakic intraocular lens 1. Thereby, the hole 6 can be easily formed in the center of the diffraction grating 5 which is formed in the lens central part 2. In addition, since the diffraction grating 5 is thin, the optical performance of the phakic intraocular lens is not impaired.

In addition, since the hole 6 formed in the center of the diffraction grating 5 is located between the iris 11 and the crystalline lens 10 at a position corresponding to the pupil, aqueous humor can easily flow from the posterior chamber 14 to the anterior chamber 13 through the gap 12 and the hole 6 formed in the center of the diffraction grating 5. The phakic intraocular lens 1 according to Embodiment 1 thus facilitates the flow of aqueous humor. The optical properties of the phakic intraocular lens 1 provided with the hole 6 are almost the same as those of a phakic intraocular lens without the hole 6.

The diffraction grating 5 can form a single focal point because the diffraction grating 5 has the grooves which are formed such that the farther an interval between the grooves is from the center of the diffraction grating 5, the smaller the interval is, the grooves being provided with the serrated portions 5A to 5C whose height D is adjusted to a predetermined value according to Formula (2). Thus, the optical performance of the phakic intraocular lens is not impaired.

Embodiment 2

Figure 8:
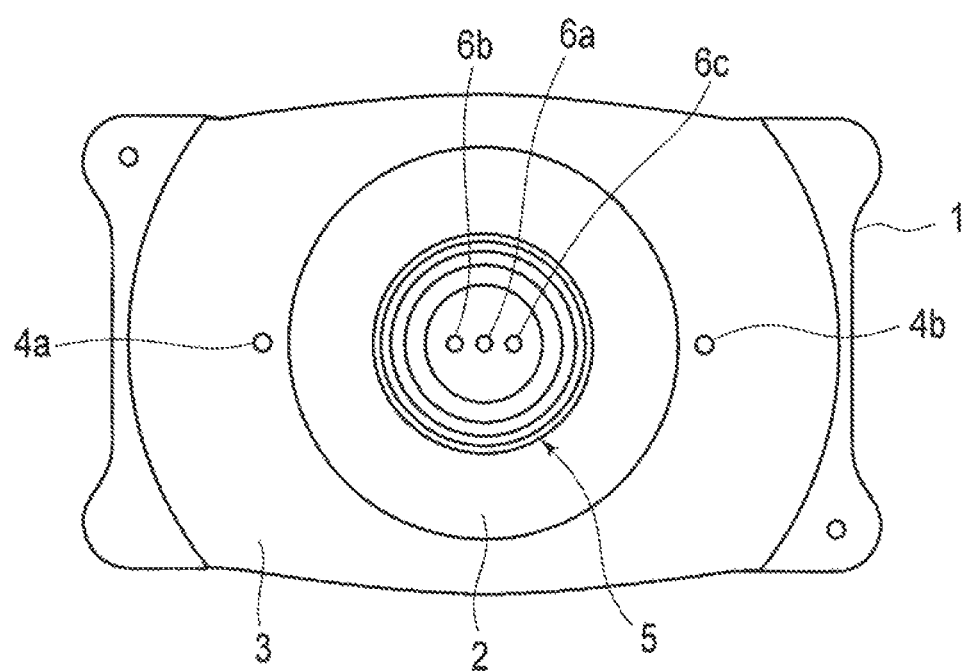
FIG. 8 is a diagram showing the configuration of a phakic intraocular lens according to Embodiment 2 of the present invention.

FIG. 8 is a diagram showing the configuration of a phakic intraocular lens according to Embodiment 2 of the present invention. The phakic intraocular lens according to Embodiment 2 shown in FIG. 8 is characterized in that three holes 6a, 6b, and 6c are provided near the center of the diffraction grating 5.

The three holes 6a, 6b, and 6c are provided within a 1.5-mm diameter circle whose center is the center of the diffraction grating 5, and are each 0.1 mm in diameter.

The phakic intraocular lens having such three holes 6a, 6b, and 6c near the center of the diffraction grating 5 can also achieve advantageous effects similar to those achieved by the phakic intraocular lens according to Embodiment 1.

Although three holes are provide within a 1.5-mm diameter circle whose center is the center of the diffraction grating 5 in Embodiment 2, two holes, for example, may be provided within a 1.5-mm diameter circle whose center is the center of the diffraction grating 5. In such a case, the two holes are each 0.15 mm in diameter.

In other words, the sum of the areas of holes in the multiple-hole case needs to be equal to or smaller than the area of a hole in the single-hole case.

INDUSTRIAL APPLICABILITY

The present invention is applicable to an intraocular lens for implantation between the iris and the crystalline lens.

The invention claimed is:
1. A phakic intraocular lens for implantation between an iris and a crystalline lens, comprising:

a diffraction grating that is disposed in a central part of the lens and has circular, coaxial grooves formed thereon, the grooves formed such that the farther an interval between grooves is from a center of the diffraction grating, the smaller the interval between grooves is, such that the diffraction grating focuses light to a single focal point, wherein the height h from a center of the diffraction grading to each coaxial groove is expressed by:

$$h=\sqrt{2Rm\lambda}$$

where $\lambda$ is the wavelength of light, R is a distance between the center of the diffraction grating and a focal point, and m is an integer representing groove number from the center of the diffraction grading; and wherein the grooves are provided with serrated portions having a height D that is adjusted to a constant value based on $D(nL-nW)\lambda$, wherein $\lambda$ is a wavelength of light, nL is an index of refraction of the diffraction grating, and nW is an index of refraction of aqueous humor; and a support part that is disposed outside the diffraction grating and supports the diffraction grating, wherein a plurality of holes are provided near the center of the diffraction grating within a 1.5 mm diameter circle whose center is the center of the diffraction grating, wherein one of the plurality of holes is formed at the center of the diffraction grating.

2. The phakic intraocular lens according to claim 1, wherein the plurality of holes comprises three holes, each hole being 0.1 mm in diameter.

3. The phakic intraocular lens according to claim 1, wherein the plurality of holes comprises two holes, each hole being 0.15 mm in diameter.

\* \* \* \* \*